United States Patent [19]

Wolf

[11] Patent Number: 5,065,751

[45] Date of Patent: Nov. 19, 1991

[54] METHOD AND APPARATUS FOR REVERSIBLY OCCLUDING A BIOLOGICAL TUBE

[76] Inventor: Gerald L. Wolf, 100 Denniston St. #77, Pittsburgh, Pa. 15206-4043

[21] Appl. No.: 589,769

[22] Filed: Sep. 28, 1990

Related U.S. Application Data

[62] Division of Ser. No. 460,314, Jan. 3, 1990, Pat. No. 4,983,177.

[51] Int. Cl.⁵ .......................... A61F 6/06; A61F 6/02
[52] U.S. Cl. .................................... 128/831; 128/843
[58] Field of Search ................ 606/157; 128/831, 834, 128/836, 843

[56] References Cited

U.S. PATENT DOCUMENTS

| | | | |
|---|---|---|---|
| 3,422,813 | 1/1969 | Bealey et al. | 128/843 |
| 3,589,355 | 6/1971 | Lee | 128/843 |
| 3,731,670 | 5/1973 | Loe | 128/1 |
| 4,200,088 | 4/1980 | Denniston, Jr. | 128/1 |
| 4,365,621 | 12/1982 | Brundin | 128/1 |
| 4,509,504 | 4/1985 | Brundin | 128/1 |
| 4,512,342 | 4/1985 | Zaneveld et al. | 128/843 |
| 4,606,336 | 8/1986 | Zeluff | 128/831 |
| 4,805,618 | 2/1989 | Ueda et al. | 128/831 |

FOREIGN PATENT DOCUMENTS

| 1113045 | 5/1989 | Japan | 128/831 |
|---|---|---|---|

OTHER PUBLICATIONS

Engineering in Medicine, vol. 6, No. 4, Oct. 1977, pp. 123-124.
Medical & Biological Engineering & Comp., vol. 18, No. 14, Jul. 1980, pp. 503-509.

Primary Examiner—Stephen C. Pallegrino
Assistant Examiner—Gary Jackson
Attorney, Agent, or Firm—Arnold B. Silverman; Rita M. Rooney

[57] ABSTRACT

A method of reversibly occluding a biological tube is provided as well as a related apparatus. The method includes providing an occluding member to be introduced into or around a biological tube thereby blocking flow through the tube. When it is desired to eliminate such blockage, shock wave lithotripsy or other energy is employed to fragment the occluding member and thus eliminate its blockage of the biological tube. The related occluding device comprises an occluding member having an inner core of a first rigid material encapsulated in an outer shell comprised of a flexible second material. The first will fragment when struck by shock waves. The device may be either a plug-type device or a C-shaped clamp. Alternatively, the device may be comprised of a single material which is introduced in flowable form into the tube by means of a catheter. The material then hardens to form a substantially rigid plug.

5 Claims, 3 Drawing Sheets

METHOD AND APPARATUS FOR REVERSIBLY OCCLUDING A BIOLOGICAL TUBE

This is a division of application Ser. No. 07/460,314, filed Jan. 3, 1990 now U.S. Pat. No. 4,983,177.

BACKGROUND OF THE INVENTION

1. Field of the Invention

This invention relates to a method and related apparatus for reversibly occluding a biological tube within a body to control the flow of matter through the tube. The method further contemplates removal of the obstruction using lithotripsy techniques to fragment the occluding device, and thereby clear the tube once again.

2. Background Information

In many applications in the medical and scientific research fields, it is necessary or desirable to arrest normal or abnormal function of a biological tube by blocking or occluding flow or passage through the tube of fluids or solids. Many procedures which have been known for occluding a body tube are discussed hereinafter. Such procedures often require surgical introduction of the occluding device into the body tube. In most cases the device cannot be removed without further surgery.

One particular field where occlusion of a body passage is important today is that of fertility limitation or sterilization. The problem encountered with the most prevalent method of both female and male sterilization is that of non-reversibility. In male sterilization, generally a vasectomy is performed by surgically severing the vas deferens. Alternatively, a method is used for tying off the vas deferens.

Similarly in female sterilization, a surgical procedure is necessary to prevent transport of ova through the oviduct. Again, either surgical severance of the oviduct is required or a tying procedure is used.

The problem, however, which is presented with both male and female sterilization is that of reversibility. The procedures currently being used are essentially non-reversible. Therefore the decision to undergo such a procedure is one from which a person cannot retreat. However, if reversibility of such procedure were to become dependable, simple and inexpensive, then more individuals may opt for these procedures as methods of fertility control.

There are also many other situations which require blocking of body passages. For example, there may be cases where surgical procedures require occlusion of a blood vessel temporarily or that fistulae or intracranial or intraspinal vascular malformations be blocked off from normally functioning vessels and ducts.

As mentioned hereinbefore, methods have been known for occlusion of body tubes. For example, various types of plugs have been known to occlude the vas deferens for blocking the flow of sperm. U.S. Pat. No. 3,422,813 discloses such a plug, however, surgical removal of the occlusion would be required.

Other methods include valves which may be introduced into such passages. See U.S. Pat. No. 3,731,670 which discloses a magnetic duct valve, and U.S. Pat. No. 4,200,088 which discloses a plug member.

Various devices have also been known which are introduced into a duct and which, after coming into contact with the water in the body, swell up and tightly fit within the body duct in which they are introduced. See U.S Pat. Nos. 4,365,621 and 4,509,504.

Other devices have been known which again, require surgical removal when they are no longer necessary or desired. See U.S. Pat. No. 4,512,342.

In spite of the foregoing attempts there remains a need for an improved method and related apparatus for occluding a biological passage or tube and, in particular, for sterilization by such occlusion, which is reversible and which does not require invasive technique for the reversal of the occlusion. There is also a need for such a method whereby the occluding device ma be introduced into the tube without the necessity of surgery.

SUMMARY OF THE INVENTION

As used herein the term "biological tube" shall refer to any tube, duct, passage or any other item not specifically mentioned which carries gas, fluids or solids in a biological system such as in humans and animals.

As used herein, "subject" means a member of the animal kingdom including humans.

The present invention provides an improved method of and related apparatus for reversibly occluding a biological tube of a subject. The method includes providing an occluding member which is introduced into the interior or secured to the exterior of a tube at a predetermined location along the biological tube such that normal transport of material through the tube is resisted.

The occluding member is comprised generally of a solid core which will fragment when struck with sonic waves. The fragmentable core may be encapsulated in an outer shell comprised of a biologically acceptable material. The occluding member can take many different forms and remain within the context of the present invention. For example, the occluding member could be a rigid material encapsulated in a flexible biomedically accepted material which forms a plug which can be introduced into the interior of the subject's body tube to be obstructed. Alternatively, the occluding member may be a generally C-shaped clamp which may be slipped over a biological tube crimping it to close it off. Alternatively, the occluding member could be comprised of a flowable material which hardens in situ. Depending upon the application, the device may be introduced into the body duct from external openings or using a catheter without the necessity of substantial surgical intervention.

When it is desired to reverse the occlusion, sonic waves are generated using a known technique referred to as "lithotripsy" which is commonly used to fragment and eliminate kidney stones. The sonic waves are directed at the occluding member to fragment at least a portion of the occluding member.

Upon exposure to such fragmenting energy, the solid inner core will crumble and allow the obstruction to be expelled or removed in the case of the internal embodiment. In the case of the generally C-shaped clamp, the inner core will crumble and allow the structure to open, thereby opening the passageway once again.

The biologically acceptable outer shell encases the solid core to protect it from biochemical reactions and body actions and, in turn, to protect the body from damage during miniature explosions which cause fragmentation. Further, the outer shell facilitates the expulsion or safe retention of the device as altered after fragmentation.

It is an object of this invention to provide a safe and reliable method of reversible occlusion of a subject's biological tube.

It is another object of the invention to provide an occluding means which is removed when shock waves using lithotripsy techniques are directed at the occluding member thereby causing it to fragment.

It is a further object of the invention to provide an occluding member which may be introduced into the biological tube at the desired location without the necessity of substantial surgery.

It is an object of the invention to provide a method of sterilization of humans or animals which is completely and safely reversible.

It is a further object of the invention to provide a method and related apparatus for occluding a biological tube, and reversing the occlusion, using known and readily available techniques and equipment.

These and other objects of the present invention will be more fully understood from the following description of the invention with reference to the illustrations appended hereto:

DESCRIPTION OF THE PREFERRED EMBODIMENTS

For simplicity of disclosure, the invention is described in the context of occlusion of a human biological tube, however, it should be understood that the invention has other applications.

Figure 1:
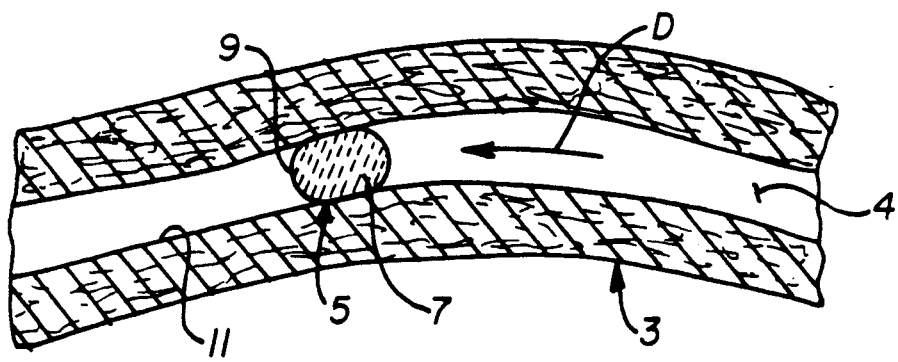
FIG. 1 is a schematic cross-sectional view of a biological tube occluded with an occluding member of the present invention.

FIG. 1 shows a portion of a body of a subject having a biological tube 3 which has passageway 4 therein through which materials flow in the direction denoted by the arrow D. Introduced into the tube 3 by methods discussed hereinafter is an occluding member 5. The occluding member 5 may be comprised of an inner core 7 made of a rigid material and preferably, it is comprised of a ceramic material.

Among the preferred ceramics for use in the solid core of the present invention are sintered calcium phosphate ceramics. These include, for example, whitlockite, hydroxyapatite, or tricalcium phosphate. One of the advantages of such materials is the ability to provide the desired porosity.

As the fragmentation is achieved by lithotripsy methods, the solid material should have an acoustic impedance much different from that of body tissue and an inherent fragility that allows it to break into many pieces upon effective exposure. This property must not be compromised by the surrounding shell or the internal struts. As these shell materials serve as an acoustic interface they could, if improperly selected, reduce the fragmenting forces of the sound waves. The materials selected are preferably fragmentable by extracorporeal shockwave lithotripsy methods, and should also be visible to medical imaging devices.

The inner core 7 of occluding member 5 may be encapsulated in an outer shell 9 which is made of a flexible, biomedically acceptable material such as silicone elastomer, polyurethane, polypropylene, polyvinyl, polytetrafluoroethylene, and polyethylene terephthalate and is preferably SILASTIC. The encasing biomedical material can be resiliently yielding or spongy to protect the biological tube. It may be permeable to allow gases generated by vaporization to escape but should not allow biological fluids or cells to reach the interstices and prematurely damage the rigidity of the fragmentable solids in core 7. The shell 9 preferably has a thickness of about 1/20 of the cross-sectional diameter of the occluding member, and generally will be less than about 1 mm. and is resiliently compressible to enhance the intimacy of seal between the interior surface 11 of the biological tube 3 and the occluding member 5.

The occluding member 5 is sized in accordance with the biological tube 3 into which it is inserted. The member 5 should be of such a size that it is tightly engaged by the interior walls 11 of the tube 3 so that undesired travel of member 5 within tube 3 is avoided. The occluding member 5 resists or prevents flow of material through the tube 3, which normally flows through in the direction D.

Figure 2:
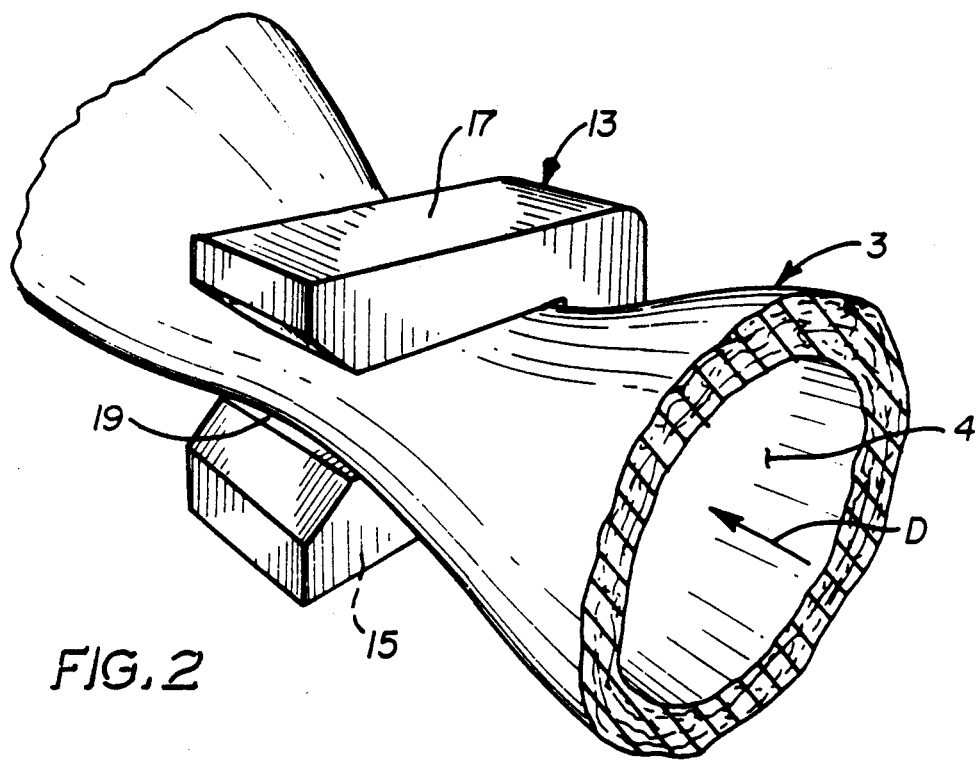
FIG. 2 is a schematic perspective view of a second embodiment of the present invention wherein the occluding member is a clamp engaged across the biological tube.
Figure 3:
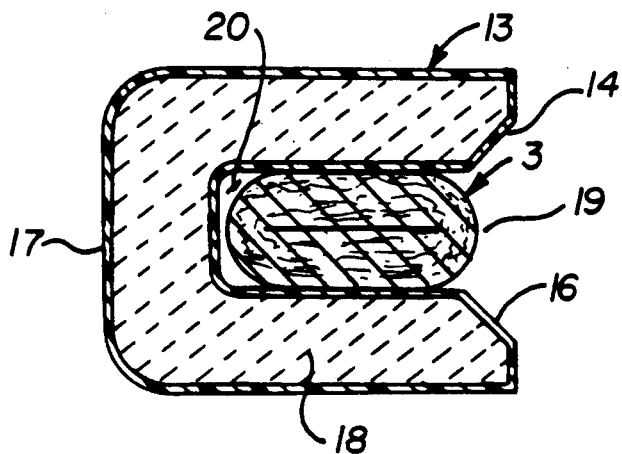
FIG. 3 is a schematic cross-sectional view of the device of FIG. 2 compressing a biological tube.

Another embodiment of the occluding device of the present invention is shown in FIGS. 2 and 3 in which a portion of a body of a subject encloses a biological tube 3, which has a passageway 4 therethrough. Positioned around the biological tube 3 is occluding member 13. The generally C-shaped occluding member 13 produces a crimp in tube 3 preventing flow through the tube 3. The occluding member 13 is comprised of an inner core 15 made of a rigid material such as a ceramic. It is encapsulated in an outer shell 17 which is composed of a flexible biomedically acceptable material. The outer shell 17 may be comprised of biologically compatible polymers such as silicone elastomer or polyurethane, for example, and is preferably made of SILASTIC. As shown in FIG. 2, the portion 19 of tube 3 which is engaged by the clamp 13 is entirely compressed so as to be closed. Thus, tube 3 is occluded and flow designated by D is resisted or prevented, as desired in the application.

The generally C-shaped clamp 13 is shown in cross section in FIG. 3. Clamp 13 occludes the tube at portion 19 thereby preventing or resisting flow as mentioned herinbefore. Clamp 13 preferably has a pair of pilot surfaces 14, 16 to facilitate introduction of tube 13 into the clamp interior. Clamp 13 may also include internal struts 18. The struts 18 can have high tensile strength to resist alteration of shape while the inner core 15 is in its original shape. For example KEVLAR or MYLAR would resist stretching when the solids are fragmented as discussed hereinafter. The struts 18 will preferably be so provided as to not resist tubular re-opening when the supporting solid is fragmented. In order to achieve this struts 18 are oriented appropriately such that they will collapse and lie co-axially along the center of the tube within the occluding clamp 13.

The material for the outer shell 17 of the clamp 13 is preferably a silicone or elastomer such as SILASTIC. These materials would be chosen to allow the clamp 13 to fragment and open up, yet they would not require that the clamp 13 be physically removed from the body. The materials for the inner core 15 could be the same as those disclosed in reference to the embodiment of FIG. 1

The gap 20 in the clamp 13 for receiving the tube 3, must assure obstruction without causing tissue damage that would elicit fibrosis or scarring which could lead to permanent occlusion of the tube 3. The gap 20 should also be such that local ischemia in the walls of the tube is avoided.

The materials in all of the embodiments should be visable by imaging techniques so that proper placement is made, and so that it is possible to periodically check to assure that the device is remaining in the desired place.

Surgical techniques could be used to introduce the clamp. Once it is in place, there are many methods for retaining the clamp in place, such as: a spring-like hinge, a snap-fit closure, a sleeve or band placed around the clamp, or an interlock applied from the other side, for example (not shown in FIG. 3).

When it is desired to remove the occluding member 5, the present invention employs the method known as "lithotripsy." Lithotripsy, more specifically entitled, extracoporeal shock wave lithotripsy ("ESWL") has been employed with great success in connection with the elimination of kidney stones. ESWL has been used to break up kidney stones without surgery.

ESWL involves generating a sonic wave that will transfer energy through biological materials. The pressure wave so produced normally has a single, sharp pressure spike of a large amplitude and gradual relaxation. It is composed of both high and low frequencies in order to transmit energy more efficiently through biological materials. A general description of the background of ESWL may be found in Staritz, et al., *Electromagnetically Generated Shock Waves for Gallstone Lithotripsy: In Vitro Experiments and Clinical Reliance*, European Journal of Clinical Investigation (1989) 19, p. 142-145, and Ebrahimi et al., *Fracture Behavior of Urinary Stones under Compression*, Journal of Biomedical Materials Research, Vol. 23, pp. 507-521 (1989).

Briefly, the waves are generated, often in water, and focused on a target, such as a kidney stone or the fragmentable occluder of the present invention. As the human body has an acoustic impedance essentially the same as water, no intensification of sonic wave occurs as it enters the human body. In addition, the sonic wave travels through the body without dissipating a significant portion of its energy. When the waves reach the target, due to a large difference in the acoustic impedance between the stone and soft tissues, enough pressure is generated to fragment the target. A series of waves will eventually shatter the target into small pieces and will effectively allow the debris to pass out of the body.

Figure 4:
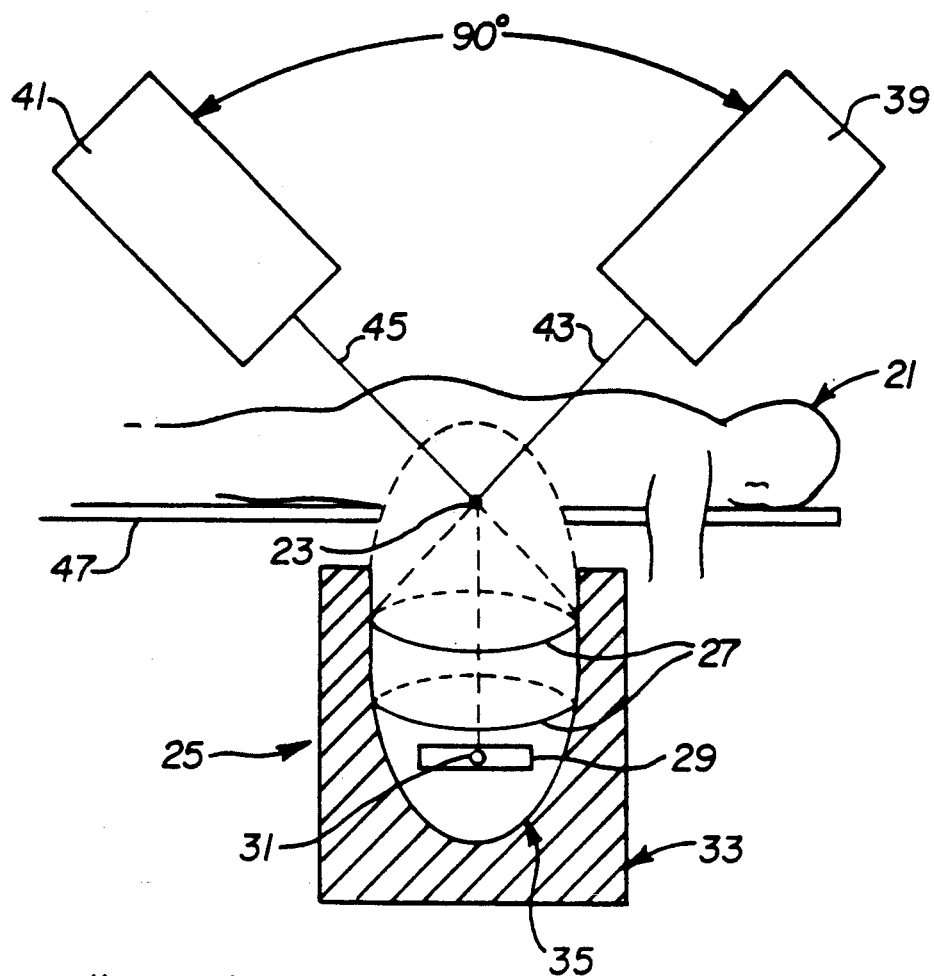
FIG. 4 is a schematic diagram of a subject undergoing the procedure of reversing the occlusion as described in the present invention.

Referring to FIG. 4, the operation of the method of the present invention employing lithotripsy techniques will be described. A subject 21 has device 23 implanted in a biological tube (not shown). A lithotriptor, generally designated as 25, is used to fragment the occluding device 23 of the present invention. Lithotriptor 25 directs a series of waves 27 towards the subject 21, and in particular, towards device 23. The waves may be generated by spark gap discharge, electromagnetic or piezoelectric methods, for example. See Delius et al, *Extracorporeal Shock Waves: Properties and Principles of Generation, Biliary Lithotripsy*, 1989, Yearbook Medical Publishers, pp. 31-42. The semi-ellipsoid 33 has an ellipsoidal surface 35 which focuses the sonic wave on the target 23. The electrode 29 is placed in the focal point 31 of ellipsoid 33. This arrangement is desirable as a sonic wave moves spherically, the energy density is reduced because the total energy is distributed over an ever-increasing sphere.

The target device 23 is placed at the second focal point of the ellipsoid. In order to find that point, it has been known to provide a set of X-ray fluoroscopes 39 and 41 or alternatively, a set of laser beam generators, which are placed generally perpendicular to one another as shown in FIG. 4. The fluoroscopes are placed such that the intersection of the respective beams 43 and 45 is at the second focal point. A monitor (not shown) will display the point of intersection on a screen superimposed on an image of the area of the body of subject 21 showing target device 23. By viewing the screen, a technician can maneuver the subject 21 on a movable table 47 to line the target up with the second focal point.

Once the patient is properly placed, a series of waves 27 will be directed at the target 23 until the pressure stress produced exceeds the strength of the occluding device, which is the target 23, and mechanical destruction thereof occurs. Generally, the patient exposure would vary with the mass of the fragmentable target, its ease of fragmentation and its position within the body.

Preferably, the waves 27 are applied until the rigid material member is sufficiently fragmented to establish the desired change in shape.

Figure 5:
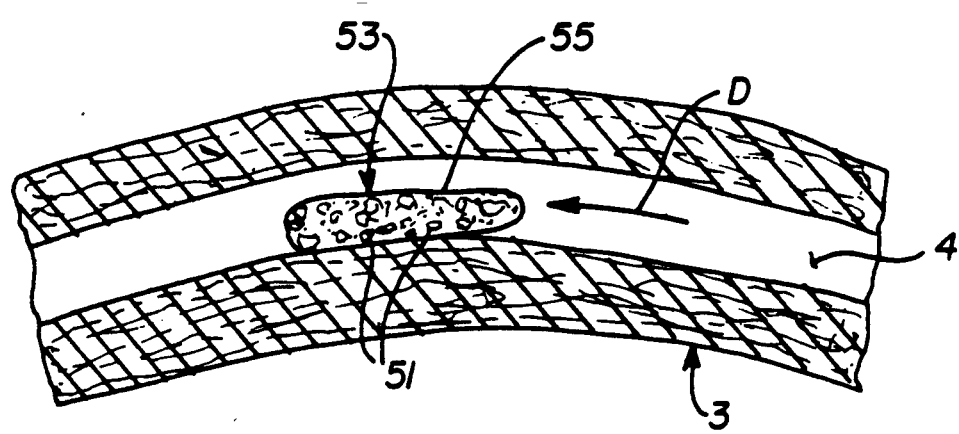
FIG. 5 is a schematic cross-sectional illustration of the device of FIG. 1 with the core of the occluding device fragmented after the lithotripsy technique is employed using the method of the present invention.

Referring to FIG. 5, fragments 51 are what remains of the inner core of the occluding member 53 after the lithotripsy method of the present method is employed. The occluding member 53 has an outer shell 55 which encases the fragments 51. The occluding member 53 is now deflated allowing passage of material within biological tube 3 in the direction D around it. The outer shell 55 is preferably comprised of an inert material and would not cause harm if it remained within the tube. Alternatively, the device could be removed surgically, noninvasively, with endoscopy or catheter techniques or it may pass out of the system under normal peristaltic forces, depending upon the application. In any of those cases, after the core of the occluding member is fragmented, material may flow freely within the biological tube and the occlusion of the tube 3 is reversed.

Figure 6:
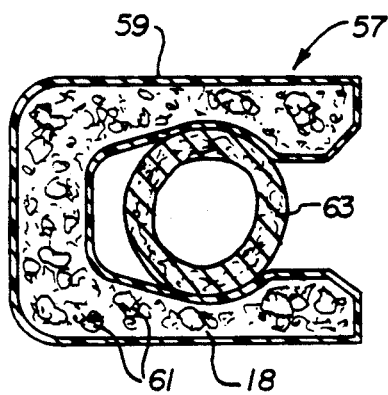
FIG. 6 is a schematic cross-sectional view of the device of FIG. 2 with the core of the C-shaped occluding device fragmented after the lithotripsy technique is employed using the method of the present invention.

Referring to FIG. 6, the C-shaped clamp is shown with its inner core having been fragmented. The clamp 57 has shell 59 which encases the plurality of fragments 61. When the inner core is fragmented, the clamp 57 opens, and tube 63 resumes its normal cross-section. In addition, where desirable, struts 18 could determine the new shape of the occluding member after fragmentation. This shape is controllable and may be predetermined for each application or material. Fluid can then flow through and the occlusion has been reversed.

In operation, the occluding member 5 of the present invention is introduced into a biological tube 3. (FIG. 1.) The occluding member 5, if it is the plug-like embodiment shown in FIG. 1, may be introduced into the body by means of a catheter using known techniques to deliver the device to the desired location. Alternatively, if the occluding member to be used in the application is the C-shape clamp occluding member 23 of FIG. 4, then it may be necessary to apply the clamp to the tube using surgical techniques under direct vision or by percutaneous methods. However, with conventional imaging or endoscopy techniques being used for guidance, minimal intervention would be required. In the alternative, a flexible material may be injected into a balloon catheter which has been positioned at the desired location.

When it is desired to remove the obstruction, ESWL is used to fragment the occluding device to clear the passageway and allow normal flow of fluids to resume.

Figure 7:
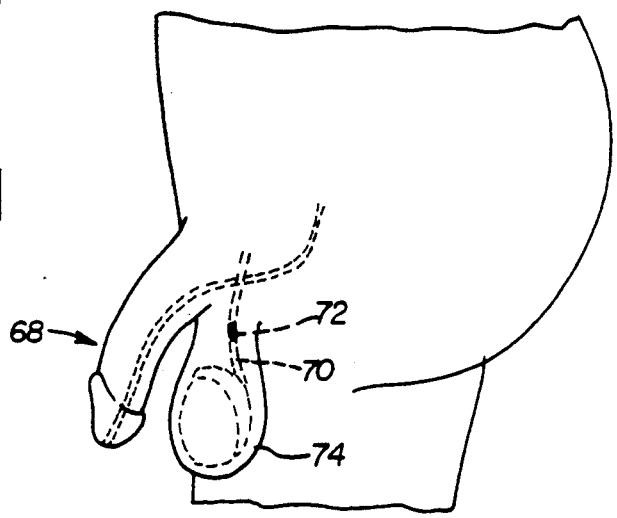
FIG. 7 is a schematic illustration of the method and related device of the present invention as used for purposes of human male sterilization.

One of the very important applications of the method and related apparatus of the present invention is that of reversible sterilization in humans or in animals. Referring to FIG. 7, wherein human male genitalia 68 is shown for purposes of describing the device as employed for male sterilization, the vas deferens 70 may be blocked by an occluding device 72 of either type, the internal or external device, in accordance with the present invention. In this application, preferably the C-shaped clamp embodiment would be employed as the occluding device. The occluding device 72 would serve to block the flow of sperm from testis 74 and thereby provide sterilization. When it is desired to reverse this effect, lithotripsy as described hereinbefore may be employed and, as a result, the sterilization can be completely reversed in a safe and reliable manner which does not require surgery.

Figure 8:
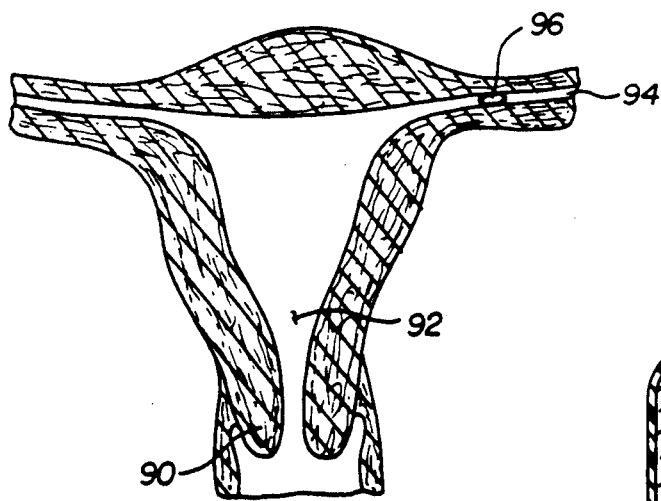
FIG. 8 is a schematic illustration of a method and related device of the present invention employed in internal female sterilization.
Figure 9:
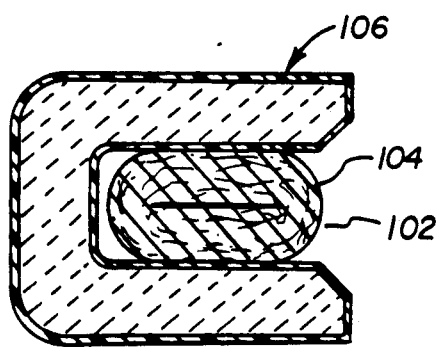
FIG. 9 is a cross-sectional illustration of a clamp of the present invention employed in external female sterilization.

Similarly an occluding device may be introduced into the oviduct to prevent the travel of ova in the fallopian tube thereby providing female sterilization. As shown in FIG. 8, the cervix 90 and uterus 92 are in communication with the fallopian tube 94 which has an occluding plug 96 of the present invention in place. In FIG. 9 the generally C-shaped clamp 100 has an opening 102 through which fallopian tube 104 enters and is clamped.

In addition, occluding devices of the present invention may be employed in blood vessels to restrict or occlude the flow of blood which may be necessary in certain applications.

The method of the present invention involves introducing an occluding device such as the device 5 of FIG. 1, for example, into a biological tube 3. The device may be introduced by surgical techniques. Alternatively, the device may be introduced through a localizing catheter or another inner catheter through which one or more materials are injected in liquid or semi-liquid form. The materials chosen for such an embodiment would be materials which would solidify into fragmentable "stones" that occlude the tube. Alternatively, a solid in powder form would be co-injected with a liquid that polymerizes in place. One or both materials would have to be visible by medical imaging techniques to ascertain appropriate placement of the materials within the tube. The catheter would be removed after solidification. The obstruction may be confirmed by diagnostic testing. The polymerizing material could remain flexible so that, upon fragmentation of the solid, the obstructing mass can be expelled or removed. The materials chosen would have to be materials which remain stationary so that obstruction would be effectively maintained without undue local tissue damage.

Alternatively, two solutions may be injected through separate catheter lumens and "solidify" on contact. And still further, a template mesh of flexible material may be initially inserted and its interstices subsequently filled with the materials described hereinbefore.

Yet another embodiment would include a detachable balloon which would be positioned at the desired location and its position verified by inflation of the balloon with a gas or liquid visible to imaging devices such as ultrasound fluoroscopy. The balloon lumen is then filled with a polymerizing fluid containing the solid crystals. Once the material has solidified and created the desired obstruction, the balloon is detached.

As discussed hereinbefore, devices such as plug type devices or C-shaped clamps could be introduced in engagement with the tube by surgical methods.

When it is desired to remove the obstruction, the method of the present invention involves applying energy such as sonic energy using lithotripsy methods, directed toward the device to fragment the device. The solids within each device would be crushed, allowing the obstruction to assume a new shape or to become moldable by reducing rigidity. Thereafter the method involves facilitating passage of the obstruction due to natural peristalsis or may be removed by catheter intervention techniques.

Whether externally applied as a clamp or internally applied as a controlled obstruction, there are many additional uses for this technology that will be obvious to those skilled in the art. For example, the device could be used for occlusion of a varicocoele to improve male fertility. In addition, the device could be used for temporary closure of a natural or artificial tract. An indwelling tract, either natural or artificial, can be closed or reopened at a later time for subsequent use.

The ability to non-invasively open a clamp could be useful for surgical or interventional devices where reversibility is desired. For example, a gastric pouch may be created by excluding a portion of the stomach with a looping ligature that is closed by a fragmentable clamp of the present invention, for example, in the case of intractable obesity. When it is desired to release the ligature, the clamp can be fragmented by lithotripsy in accordance with the method of the present invention. Alternatively, a balloon may be inflated in a lumenal location such as the stomach and the inflating liquid or gas could be sealed in with a fragmentable occluder. Subsequently, the balloon can be deflated by releasing the occlusion by way of lithotripsy as discussed hereinbefore.

It should also be understood that the occluding material and the device releasing the occlusion may be other than lithotripsy and lithotripsy-sensitive solids as discussed herein. For example, other forms of shock waves could be used and would be effective upon the identified or other materials.

It should be understood that there are many different situations in which a biological tube in humans or in animals must be occluded for a variety of reasons and the method and related apparatus of the present invention can be safely and easily employed in most such circumstances. The examples given are exemplary only and do not restrict the present invention to the specific examples cited. More specifically, while for purposes of illustration, generally oval plugs or C-shaped clamps are shown, other shapes may be employed, if desired.

It will be appreciated that the method and apparatus of the present invention provides reversible occlusion of biological tubes and this is accomplished in a safe and reliable manner without the necessity of surgical intervention because the device would be fractured and then would either remain in place in non-obstructing form or would pass from the system.

Whereas particular embodiments the present invention have been described above for purposes of illustration, it will be appreciated by those skilled in the art that numerous variations of the details may be made without departing from the invention as described in the appended claims.

What is claimed is:

1. A method of forming an occlusion member in a biological tube reversibly blocking passage of material through said tube, including the steps of:
   selecting a material fragmentable by shock wave;
   establishing said occlusion member in said tube by introducing said material into said tube in flowable form; and
   allowing said material to harden in situ thereby occluding said tube.

2. The method of claim 1 including
   disposing said occlusion member in a predetermined position within said tube.

3. The method of claim 2 including
   reversing occlusion of said tube by directing shock waves at said occlusion member to fragment said occlusion member.

4. The method of claim 3 including
   introducing said material by injecting by catheter a mixture of a solid material in powder form and a liquid that will polymerize in situ thereby inducing solidification; and
   removing said catheter after solidification takes place.

5. The method of claim 3 including
   introducing said material by inserting a first catheter lumen containing a first material into said tube;
   inserting a second catheter lumen containing a second material into said tube; and
   providing as said first and second materials substances which will solidify on contact with one another.

* * * * *